United States Patent [19]

May et al.

[11] 4,419,114

[45] Dec. 6, 1983

[54] SYSTEM AND METHOD FOR CONVERTING WELLHEAD GAS TO LIQUEFIED PETROLEUM GASES (LPG)

[75] Inventors: Ronald L. May, Humble; Nicholas J. Snow, Jr., Houston, both of Tex.

[73] Assignee: Sappsucker, Inc., Houston, Tex.

[21] Appl. No.: 369,159

[22] Filed: Apr. 19, 1982

[51] Int. Cl.³ .............................. F25J 3/00; F25J 5/00
[52] U.S. Cl. ............................................ 62/17; 62/20; 62/21; 62/26; 62/30; 62/37; 62/40; 62/41
[58] Field of Search .................... 62/9, 11, 17, 19, 20, 62/21, 23, 26, 30, 37, 40, 41; 55/27, 29, 30, 40-43, 68

[56] References Cited

U.S. PATENT DOCUMENTS

| | | | |
|---|---|---|---|
| 2,198,098 | 4/1940 | Vaughan | 62/23 |
| 2,217,749 | 10/1940 | Hewitt | 62/23 |
| 2,814,936 | 12/1957 | Morrison | 62/9 |
| 2,896,414 | 7/1959 | Tung | 62/11 |
| 2,900,796 | 8/1959 | Morrison | 62/11 |
| 3,791,157 | 2/1974 | Tracy et al. | 62/41 |

*Primary Examiner*—Frank Sever
*Attorney, Agent, or Firm*—Bill B. Berryhill

[57] ABSTRACT

A method of converting natural wellhead gas to liquefied petroleum gases (LPG) may comprise the steps of: separating natural gas from petroleum fluids exiting a well-head; compressing the natural gas; refrigerating the natural gas, liquefying at least a portion thereof; and separating LPG from gas vapors of the refrigerated natural gas. A system for performing the method may comprise: a two-stage gas compressor connected to the wellhead; a refrigeration unit downstream of the gas compressor for cooling the compressed gases therefrom; and a product separator downstream of the refrigeration unit for receiving cooled and compressed gases discharged from the refrigeration unit and separating LPG therein from gases remaining in vapor form.

20 Claims, 1 Drawing Figure

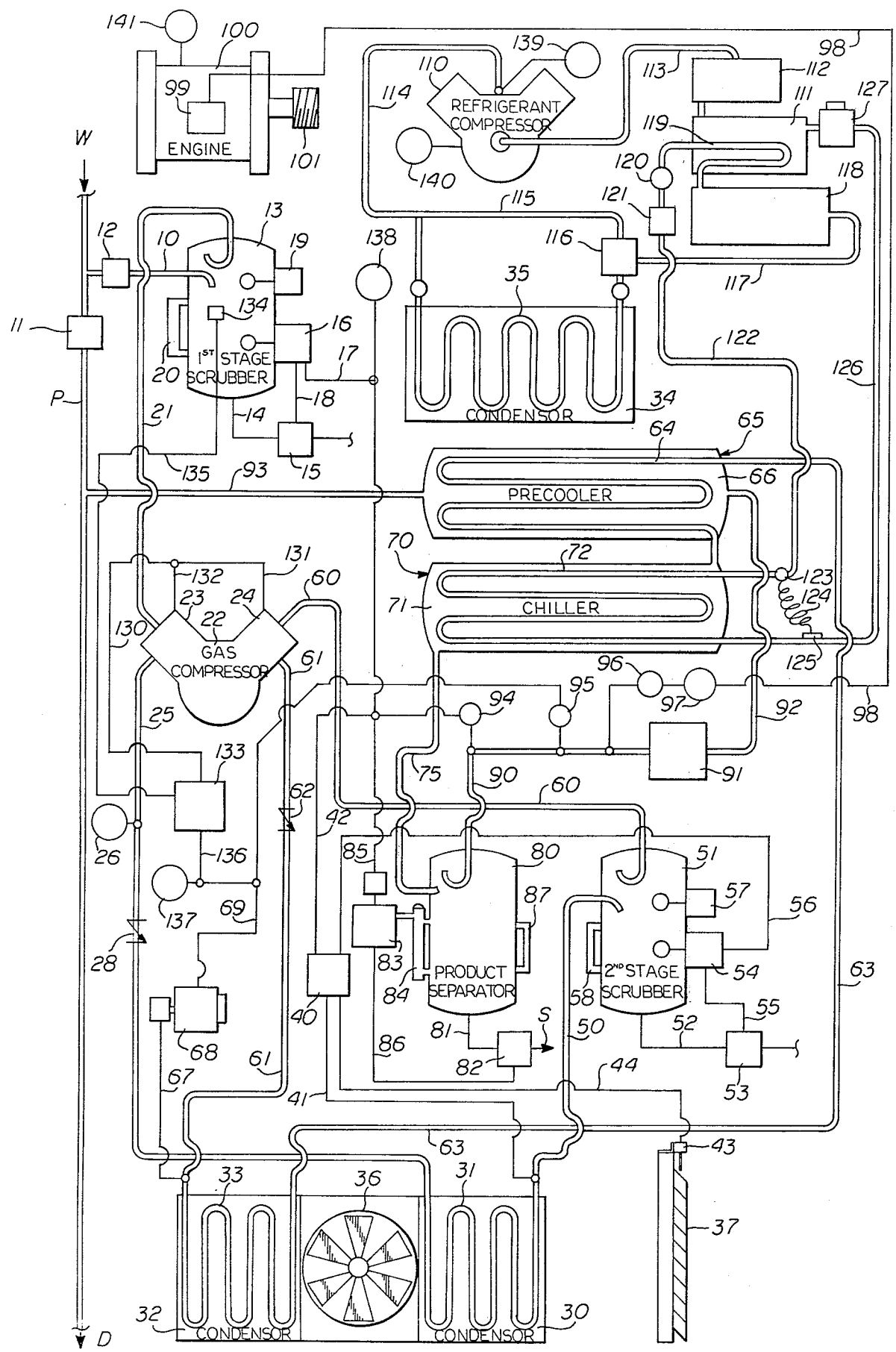

SYSTEM AND METHOD FOR CONVERTING WELLHEAD GAS TO LIQUEFIED PETROLEUM GASES (LPG)

BACKGROUND OF THE INVENTION

1. Field of the Invention

The present invention pertains to methods and systems for the production of liquefied petroleum gases (LPG). Specifically, it pertains to systems and methods for converting natural wellhead gas to LPG.

2. Brief Description of the Prior Art

Gas wells of sufficient volume are normally connected to a gas pipeline for transporting the naltural gas to natural gas markets. While the gas may be separated from hydrocarbon liquids exiting the well and dried, it is basically left in its natural form for such transportation to market.

Some natural gases may be converted to liquified petroleum gas (LPG). The primary advantage of LPG is its ability to be transferred by truck or rail to ultimate points of use not capable of supporting a pipeline. For example, LPG is widely used on farms for heating, crop-drying and dehydration, tobacco-drying, flame cultivation, irrigation pumps, cotton grinning and stationary engine operations. In addition, many farmers use LPG to operate their tractors. Many buses, trucks, forklifts and the like use LPG engines.

Large industrial and manufacturing companies have found LPG to be an answer to heating problems because of its high purity, constant quality and competitive costs as compared with other types of gaseous and liquid fuels. Many small city gas plants utilize LPG. Refineries may use LPG in the manufacture of various grades of gasoline and high-octane motor fuels. LPG is used as basic raw material in the manufacture of many plastic synthetic fibers, synthetic rubber, ect.

In recent years, gas wells which were isolated or otherwise not easily connected to a gas pipeline have been provided with processing units for converting the natural gas to LPG. Thus, the LPG produced thereby can be stored in a tank for transportation by truck or railcar. However, such processing units usually require gas production is excess of 1000 MCFD. This eliminates many wells which produce less than 1000 MCFD. Thus, such wells must be either shut-in or, if produced for their liquid hydrocarbon content, must be flared, wasting the gas produced thereby.

SUMMARY OF THE INVENTION

In the present invention, a system and method are disclosed for converting natural wellhead gas to LPG. The term "natural wellhead gas" as used herein refers also to "casing head" or "residue" gas. The method and system of the present invention are specifically designed for wells producing less than 1000 MCFD. Thus, previously uneconomical wells may be produced so as to contribute to solving the current energy shortage while producing significant income to the well owner and the gas processor.

The system may comprise a gas compressor connected to the wellhead for compressing natural gases received therefrom, refrigeration means downstream of the gas compressor for cooling the compressed gases therefrom and product separator means downstream of the refrigeration means for receiving cooled and compressed gases discharged from the refrigeration means and separating LPG therein from gases remaining in vapor form. A storage tank may be provided for receiving LPG exiting from the product separator means for storing the LPG under pressure therein. The system is especially characterized by providing means for unloading the gas compressor in the event of its suction pressure falling below a predetermined level. Thus, the system is continuously operable, even when incoming pressures fall below a safe level, e.g. 2 psig. The gas compressor simply cycles or idles under such a condition, preventing buildup of temperatures or entry of air into the system which might well occur without such an unloading means and if such did occur could cause hazardous explosions.

The system and method of the present ivention are relatively simple and compact. The system can be manufactured on a unitized skid suitable for transportation by truck or rail for easy installation at a wellhead. Power for the entire system may be supplied by a natural gas engine driven by gas supplied by the system itself. Thus, natural gas which has been previously uneconomical for production is recovered or can be recovered and converted to LPG for easy storage and transportation. Specifically, wells producing natural gas below 1000 MCFD, not previously producible, can be made to contribute to solving our energy shortage and to the economic wellbeing of the well owners and the processors. Many other objects and advantages of the invention will be seen from reading the specification which follows in conjunction with the accompanying drawing.

DESCRIPTION OF THE DRAWING

The drawing is a schematic flow diagram illustrating the system and method for converting natural wellhead gas to LPG according to a preferred embodiment of the invention.

DESCRIPTION OF A PREFERRED EMBODIMENT

Referring to the schematic flow diagram of the drawing, the system and method of converting natural wellhead gas to LPG containing propane, butane and petroleum gases of lesser vapor pressures will be described. Natural wellhead gas from a wellhead W is introduced into the system through an intake pipe 10 connected to pipeline P. The pipeline P continues past intake line 10 for eventual discharge at D into a gas gathering line or some other means for distributing gas bypassing the system and gaseous vapors exiting from the system after separation of LPG gases therefrom. A back pressure regulator 11 may be installed in the pipeline P for maintaining pressure in the pipeline P upstream thereof at some predetermined level, e.g. 22 psig. A safety shut-down valve 12 is placed in the intake line 10 and designed for failsafe closing in the event power for operating the various components of the sytem is interrupted or lost.

The natural wellhead gas entering the system may contain both natural gas and petroleum liquids. In fact, most all gas wells produce some amount of hydrocarbon liquids. The term "natural wellhead gas" as used in the specification and claims refers to any such gas, whether it is called "wellhead gas", "casing head gas", "residue gas" or the like. The natural wellhead gas entering the system through intake pipe 10 first passes through a first stage scrubber 13 whereby any petroleum liquids are separated from natural gases and collected in the lower portion thereof. Connected to the bottom of the first stage scrubber 13 is a dump line 14 and dump valve 15, which is normally in the closed position. Upon liquids reaching a predetermined level in the scrubber 13, a liquid level control device 16 introduced pressurized gas from a supply line 17 through conduit 18 to the dump valve 15, causing the valve to be opened and allowing fluids to flow through the dump line 14 for discharge to waste or other point of collection. A high level shutdown device 19 may be provided to shut the system down in the event the first stage scrubber 13 does not dump properly. A sight gauge 20 may be provided for visual observation of the level of liquids in the first stage scrubber 13.

The natural gases which are separated from hydrocarbon liquids within the first stage scrubber 13 are discharged through a line 21 for introduction into the suction side of the first stage of a two-stage gas compressor 22, the first stage of which is indicated at 23 and the second stage of which is indicated at 24. In the first stage of the gas compressor 22, the natural gas is compressed at a compression ratio of preferably 4:1. Thus, gas entering the first stage 23, e.g. at 10 psig (assuming atmospheric pressure of 14.5 psi) exits at a pressure of 83.5 psig. The compressed gas exits from the first stage 23 of the gas compressor 22 and is discharged through line 25. Discharge pressure may be monitored by a pressure gauge 26 connected to discharge conduit 25. A check valve 28 prevents reverse flow in the line 25.

Of course, when gas is compressed, its temperature increases and the discharge temperature at the first stage of the gas compressor 22 can be expected to rise to 125°-140° F. To reduce the temperature of the compressed gas, it is routed to the coils 31 of a condenser 30. The condenser 30 is actually part of a larger condenser assembly made up of the first condenser 30, second condenser 32 and third condenser 34. These condensers are cooled by air passing across the coils 31 and 33 and 35 from a fan or blower 36. The first two condensers 30 and 32 are for cooling the natural wellhead gases being processed by the system, while the third condenser 34 is for cooling refrigerant as will be more fully understood hereafter.

The cooling taking place in the condenser is extremely efficient. In fact, gas entering the first condensor 30 at 125°-140° F. will be cooled almost to atmospheric temperature. Thus, when atmospheric temperature is low, some means should be provided to prevent the gas from being cooled to the freezing point of some of the components therein. Thus, an air damper 37 may be provided for installation between the blower 36 and condenser 30 to control the amount of air passing across the coils 31. The damper 37 may be automatically adjusted by a controller 40 which receives discharge temperature information from the condenser 30 by way of conduit 41. Gas pressure from a supply line 42 is then supplied to a gas pressurized operator 43 via conduit 44 to move the air damper 37 to positions restricting or increasing the flow of air, as needed.

The cooled gases leaving the condenser 30 travel via line 50 to a second stage scrubber 51 where any liquids therein are separated from gases remaining in vapor form. The liquids separated at this point are generally natural gasolines. The natural gasolines collected in the second stage scrubber 51 are discharged through the discharge line 52 when a gas operated valve 53 is opened. The valve 53 is controlled by a pressurized gas monitored through a liquid level control device 54 from gas supply line 56 through conduit 55. Like the first stage scrubber 13, the second stage scrubber 51 may also be provided with a high liquid level shutdown device 57 and a liquid level sight gauge 58.

The gases separated from the liquids in the second stage scrubber 51 pass through line 60 to the suction side of the second stage 24 of the gas compressor 22. Here the gases are again compressed at a compression ratio of 4:1, exiting from the second stage of the gas compressor 22 at maximum pressures of approximately 300 psig. The compressed gases then pass through line 61 and check valve 62 to the second condenser 32 for cooling therein. Methanol or some other anti-freeze solution may be introduced into the gas stream at the inlet side of condenser 32 to prevent freezing in the system. The methanol may be introduced through conduit 67 by an injection pump 68 powered by gas through conduit 69.

The partially cooled gases exiting from the condenser 32 then pass through the line 63 through the tube side 64 of a shell and tube precooler 65. The shell side 66 of the precooler 65 contains gases at lower temperatures, as will be more fully understood hereafter. Thus, heat exchange takes place, raising the temperature of the gases in the shell side 66 and further lowering the temperature of the gases in the tube side 64. From the tube side 64 of the precooler 65, the gases pass to the shell side 71 of a chiller 70 which makes up a part of a refrigeration system to be more fully described hereafter. The gas is further cooled in the chiller 70 and exits through the conduit 75 into a product separator 80.

By the time the gases reach the product separator 80, they have been cooled to a range of approximately 0° F. to −20° F. and are at a pressure of approximately 250 psig to 300 psig. Under these conditions, propanes, butanes, etc., exist in liquid form (LPG). The LPG gas collected in the product separator 80 can then be transferred through the discharge line 81 via discharge valve 82 to a storage tank S (not shonw) for storage and eventual use or transfer to some other point of use. Operation of the valve 82 is controlled by a control device 83 and a specific gravity dispacement valve 84, introducing gas for operation of the valve 82 from a gas supply line 85 via conduit 86. A liquid level sight gauge 87 may also be provided.

The cold gases remaining in vapor form in the product separator 80 then exit through line 90, regulator valve 91 and line 92 passing through the shell side 66 of the precooler 65 for heat exchange, as was previously mentioned, with the gases passing through the tube side 64 of the precooler 65. The regulator valve 91 maintains a discharge pressure of approximately 250 psig. After passing through the precooler 65, the cold gas is discharged via line 93 back into the pipeline P for transportation downstream D. The cold gas being discharged through the line 93 has most of the LPG gases removed therefrom and is primarily methane and ethane.

The gases exiting from the product separator 80 at line 90 are dry and at a pressure of approximately 250 psig. This gas is useful in supplying the pressure and gases needed for operation of various other components of the system. Thus, various pressure regulators 94, 95, 96 and 97 are connected to the line 90 for supplying such gas at required pressures. For example, the regulator 94 may be set at 30 psig, regulator 95 at 60 psig and regulator 96 at 10 psig. The regulator 97 is set for approximately ten inches of water to control gas passing through conduit 98 to the carburetor 99 of a natural gas engine 100.

The natural gas engine 100 supplies power to the gas compressor 22, blower 36, refrigerant compressor 110 and other components of the system. These components may be driven from various belts and other coupling apparatus (not shown) engaging coupling 101 of some type attached to the drive shaft of the engine 100.

Referring now to the upper righthand portion of the drawing, the refrigeration unit of the system of the present invention, of which the chiller 70 and refrigerant compressor 110 form a part, will be more fully described. Beginning at a suction accumulator 111, refrigerant in vapor form passes through a suction filter or dryer 112 and intake line 113 into the refrigerant compressor 110. The refrigerant is compressed into liquid form and discharged through the discharge line 114 and passes through the coils 35 of condenser 34 for cooling of the refrigerant. The condenser 34 is actually placed near the other condenser 30 and 32 and blower 36. A bypass line 115 and headmaster control valve 116 is provided to control cooling of the refrigerant to within several degrees of the desired temperature. For example, if the refrigerant is being cooled too much, a portion of the gases are bypassed through the bypass 115. If the refrigerant is not cooled enough, more will be passed through the coils 35. The partially cooled refrigerant then passes through conduit 117 into a receiver 118 and may, via a loop 119, pass through the suction accumulator 111 for heat exchange with any refrigerant which remains in liquid form in the suction accumulator 111. Thus, it is assured that the refrigerant on the suction side of the refrigerant compressor 110 is in the vapor form.

The compressed liquid refrigerant passes from the loop 119, through a sight glass 120, filter dryer 121 and conduit 122 to an expansion valve 123. The compressed refrigerant expands through the expansion valve 123 being transformed from a liquid state to a vapor state. As is well known from the principles of refrigeration, the expansion produces gas of extremely low temperature, e.g. −20° F. The vaporized refrigerant then passes through the tube size 72 of the chiller 70 for heat exchange with the wellhead gases on the shell side 71 of the chiller 70. As previously mentioned, wellhead gases are thus cooled to a point required for separation of LPG gases in the product separator 80. The refrigerant vapors then pass from the chiller 70 via conduit 126 back to the suction accumulator 111. An evaporator pressure regulator valve 127 is provided to control system temperature to prevent freezing of the refrigerant. The evaporator valve 123 is connected to a temperature device 125 via a capillary tube 124 to provide regulation of the evaporator valve 123 responsive to the temperature of the refrigerant leaving the chiller 70.

A very important aspect of the system of the present invention is the provision of means for unloading the gas compressor 22 in the event of low suction pressure. For example, if the suction pressure at the first stage 23 of the gas compressor 22 were to fall substantially below 2 psig, there would be substantial danger of increased temperatures and the possibility of air being drawn into the system causing a fire or explosion. To prevent this, the gas compressor 22 of the present invention is provided with gas-operated unloaders which upon the occurrence of low pressures on the suction side of the system, cause the suction valves of the first and second stages 23, 24, of the gas compressor 22 to remain open, allowing the gas compressor 22 to essentially cycle or idle without compressing any gases therein. Thus, temperatures are not increased and air is not allowed to be drawn into the system. The gas operated unloaders are attached to the respective stages of the gas compressor 22 for operation by gas pressure supplied through gas lines 130, 131, and 132. Installed in the gas line 130 is a solenoid valve 133 which is normally in the closed position preventing operating gas from being supplied to the unloaders. However, upon occurrence of a predetermined low pressure, e.g. 2 psig, at a pressure device 134 located in the first stage scrubber 13, the solenoid valve 133 is actuated in response to a signal through line 135, causing the valve 133 to be opened and allowing gas to flow to the unloaders via supply line 136 connected to the regulator 95. When the pressure rises again the unloaders are deactivated.

Pressures of the system may be monitored by pressure indicators. Gas pressures at the solenoid valve 132 is monitored by pressure indicator 137. Gas pressure indicator 138 indicates pressure of gas supplied to conduits 17, 42 and 85 from the regulator 94. Pressure indicators 139 and 140 monitor the discharge and suction pressure, respectively, of the refrigerant compressor 110. Pressure gauge 141 monitors the oil pressure of the gas engine 100. Of course, other pressure and temperature indicators may be utilized for monitoring critical conditions.

Thus, the present invention comprises a system and method for converting natural wellhead gas (including casing head gas and residue gas) to LPG, including the steps of: separating natural gas from petroleum fluids exiting at a well head; compressing the natural gas; refrigerating the compressed natural gas to liquefy at least a portion thereof; and separating LPG from the refrigerated compressed natural gas. The system for performing the method includes scrubbers, condensers, compressors, separators, refrigeration systems and other apparatus connected together in a unique fashion to economically convert natural gas from a well, preferably producing at a rate of less than 1000 MCFD, to LPG. Of course, the conversion rate of natural gas to LPG will vary depending on the composition of the wellhead gas.

Not only does the present invention allow production of LPG from natural gas, it also may provide dry pressurized gas for operation of a natural gas engine supplying power for the system and may provide dry pressurized gas to the well operator for operation of other well equipment. This eliminates operators having to purchase LPG for operation of equipment, as was sometimes required in the past. Of course, the system could also be powered by an electric motor or any other suitable power source.

While a single embodiment of the invention has been described herein, many variations thereof may be made without departing from the spirit of the invention. Accordingly, it is intended that the scope of the invention be limited only by the claims which follow.

We claim:

1. A system for converting natural wellhead gas to liquefied petroleum gases (LPG) containing propane and petroleum gases of lesser vapor pressure comprising components sized and designed to process wells producing less than 1000 MCFD, including: two-stage gas compressor connected to said wellhead for compressing natural gases received therefrom; refrigeration means downstream of said gas compressor for cooling the compressed gases therefrom; product separator means downstream of said refrigeration means for receiving cooled and compressed gases discharged from said refrigeration means and separating LPG therein from gases remaining in vapor form; and means to enable said compressor to essentially cycle or idle without any gases therein, responsive to means for predetermining pressures on the suction side of said compressor.

2. A system for converting natural wellhead gas to liquefied petroleum gases (LPG) as set forth in claim 1 including first scrubber means upstream of said gas compressor and second scrubber means between the first and second stages of said gas compressor for removing any liquids from said wellhead gas which might be harmful to said gas compressor.

3. A system for converting natural wellhead gas to LPG as set forth in claim 2 including condenser means through at least a portion of which gases compressed by said first stage of said gas compressor passes prior to passing through said second scrubber means and through another portion of which gases compressed by said second stage of said gas compressor pass prior to passage through said refrigeration means.

4. A system for converting natural wellhead gas to LPG as set forth in claim 3 in which said condensor means includes an air blower providing ambient air for cooling of said compressed gases in said condenser means.

5. A system for converting natural wellhead gas to LPG as set forth in claim 4 including power means connected to said gas compressor, said refrigeration system and said condensor blower for supplying power thereto.

6. A system for converting natural wellhead gas to LPG as set forth in claim 5 in which said power means includes a gas driven engine, the gas for which is supplied by gaseous vapors separated in said product separator means.

7. A system for converting natural wellhead gas to LPG as set forth in claim 1 in which said refrigeration means includes a shell and tube chiller through which compressed gases from said gas compressor pass for heat exchange with refrigerant therein prior to being received by said product separator means.

8. A system for converting natural wellhead gas to LPG as set forth in claim 7 in which said refrigeration means includes a refrigerant compressor for receiving refrigerant from said shell and tube chiller, compressing said refrigerant, and recirculating said compressed refrigerant to said shell and tube chiller for said heat exchange with said compressed gases therein.

9. A system for converting natural wellhead gas to LPG as set forth in claim 8 in which said refrigeration means includes a condenser through which said refrigerant passes downstream of said shell and tube chiller prior to being received by said refrigerant compressor.

10. A system for converting natural wellhead gas to LPG as set forth in claim 8 including a shell and tube precooler through which said compressed gases from said gas compressor passes prior to said passing through said shell and tube chiller for heat exchange with said gases remaining in vapor form separated by said product separator means.

11. A system for converting natural wellhead gas to LPG as set forth in claim 1 in which said means for unloading said gas compressor comprises apparatus connected to the suction valves of said first and second stages of said gas compressor in communication with gaseous vapors discharged from said product separator means for operation thereof in response to said suction pressure of said gas compressor falling below said predetermined level.

12. A system for converting natural wellhead gas to LPG as set forth in claim 11 in which said means for unloading said gas compressor includes an unloader valve through which said gaseous vapors discharged from said product separator means must pass for operation of said gas compressor suction valve unloader apparatus, said valve being closed when said suction pressures of said gas compressor are above said predetermined level, preventing unloading of said gas compressor.

13. A method of converting natural wellhead gas to liquefied petroleum gases (LPG) containing propane and petroleum gases of lesser vapor pressures comprising the steps of:
separating natural gas from petroleum fluids exiting at a wellhead producing less than 1000 MCFD;
compressing said natural gas in the first stage of a two-stage gas compressor;
providing means to enable said compressor to essentially cycle or idle without any gases therein, responsive to predetermined pressures on the suction side of said compressor;
cooling said compressed natural gas;
further compressing said natural gas in the second stage of a two-stage gas compressor;
cooling said further compressed natural gas;
refrigerating said further compressed natural gas, liquefying at least a portion thereof; and
separating LPG from gas vapors of said refrigerated natural gas.

14. A method of converting natural wellhead gas to LPG as set forth in claim 13 in which said two-stage gas compressor is provided with means for unloading said gas compressor in the event of its suction pressure falling below a predetermined level.

15. A method of converting natural wellhead gas to LPG as set forth in claim 13 in which said refrigerating of said further compressed natural gas is accomplished by passing said further compressed natural gas through a chiller for heat exchange with a refrigerant therein.

16. A method of converting natural wellhead gas to LPG as set forth in claim 15 in which said refrigerant is compressed into liquid form by a refrigerant compressor, partially cooled by condenser means and expanded through an expansion valve into vapor form prior to passing through said chiller.

17. A method of converting natural wellhead gas to LPG as set forth in claim 15 in which said separating LPG from gas vapors of said refrigerated natural gas is accomplished in a product separator in which said LPG is collected for further handling and from which said gas vapors of said refrigerated natural gas pass for further use.

18. A method of converting natural wellhead gas to LPG as set forth in clam 17 in which said further compressed natural gas passes through a precooler, prior to passing through said chiller, for heat exchange with said gas vapors of said refrigerated natural gas passing from said product separator.

19. A method of converting natural wellhead gas to LPG as set forth in claim 13 in which said natural gas is compressed by said two-stage gas compressor to a pressure of at least 200 psig.

20. A method of converting natural wellhead gas to LPG as set forth in claim 19 in which said refrigerating of said further compressed natural gas cools said natural gas to a temperature of approximately 0° F. to −20° F.

* * * * *